United States Patent [19]

Cooper

[11] Patent Number: 5,399,728
[45] Date of Patent: Mar. 21, 1995

[54] PROCESS FOR THE PREPARATION OF HIGHLY ESTERIFIED ALKOXYLATED POLYOL COMPOSITIONS

[75] Inventor: Charles F. Cooper, Paoli, Pa.

[73] Assignees: ARCO Chemical Technology, L.P., Greenville, Del.; CPC International Inc., Englewood Cliffs, N.J.

[21] Appl. No.: 44,446

[22] Filed: Apr. 5, 1993

[51] Int. Cl.⁶ .......................................... C07C 51/367
[52] U.S. Cl. .................................. 554/149; 554/148; 536/18.6
[58] Field of Search .................................. 554/149

[56] References Cited

U.S. PATENT DOCUMENTS

| | | | |
|---|---|---|---|
| 2,678,935 | 5/1954 | Sundberg et al. | 554/149 |
| 3,435,024 | 3/1989 | Nobile et al. | 536/18.2 |
| 4,022,808 | 5/1977 | Yoshihara et al. | 554/149 |
| 4,115,415 | 9/1978 | Yoshihara et al. | 554/149 |
| 4,600,539 | 7/1986 | Hoppe et al. | 514/785 |
| 4,681,900 | 7/1987 | Iwasaki | 514/786 |

FOREIGN PATENT DOCUMENTS

| | | |
|---|---|---|
| 660601 | 7/1965 | Belgium . |
| 89-105357.1 | 10/1989 | European Pat. Off. . |
| 0516099 | 12/1992 | European Pat. Off. . |
| 46-10409 | 3/1971 | Japan . |
| 49-10433 | 3/1974 | Japan . |
| WO93/04030 | 3/1993 | WIPO . |

*Primary Examiner*—José G. Dees
*Assistant Examiner*—Dwayne C. Jones
*Attorney, Agent, or Firm*—Stephen D. Harper

[57] ABSTRACT

A convenient method of obtaining useful highly esterified alkoxylated polyol fat substitutes from readily available triglycerides such as fats and oils is provided.

23 Claims, No Drawings

PROCESS FOR THE PREPARATION OF HIGHLY ESTERIFIED ALKOXYLATED POLYOL COMPOSITIONS

FIELD OF THE INVENTION

This invention is related to methods for obtaining highly esterified alkoxylated polyol compositions useful as reduced calorie fat substitutes from naturally occurring triglycerides such as fats and oils.

BACKGROUND OF THE INVENTION

A wide variety of substances have been proposed for use as fat substitutes in food compositions. The chemical structures of such substances are selected such that they are more resistant to breakdown by the metabolic processes of the human digestive system which normally occur upon ingestion of conventional triglyceride lipids. Because of their increased resistance to digestion and absorption, the number of calories per gram available from the fat substitutes is considerably reduced as compared to common vegetable oils, animal fats, and other lipids. The use of such substances thus enables the preparation of reduced calorie food compositions useful in the control of body weight.

U.S. Pat. No. 4,861,613 describes one class of particularly useful fat substitutes wherein a polyol such as glycerin is alkoxylated with an epoxide such as propylene oxide and then esterified with any of a number of fatty acids or fatty acid equivalents to form an esterified alkoxylated polyol. Generally speaking, it is desirable to accomplish nearly complete esterification (i.e., to react at least 95% of the hydroxyl groups of the alkoxylated polyol intermediate with fatty acid). These substances have the physical and organoleptic properties of conventional triglyceride lipids, yet are significantly lower in available (absorbed) calories than edible oils owing to their pronounced resistance towards pancreatic lipase enzymatic hydrolysis. The thermal and oxidative stability of the esterified alkoxylated polyols renders them especially suitable for use in the preparation of reduced calorie food compositions requiring exposure to high temperatures.

The methods developed to date for the preparation of esterified alkoxylated polyol fat substitutes of this type have largely required multi-step procedures when a naturally occurring triglyceride is to be utilized as the source of the long chain acyl groups incorporated into the esterified alkoxylated polyol. The triglyceride is first hydrolytically split into glycerin (which may be employed as the polyol component) and a mixture of fatty acids. The fatty acids may be either used in an esterification reaction with an alkoxylated polyol without further modification (as described in U.S. Pat. No. 4,983,329), or first converted into $C_1$–$C_4$ alkyl esters (as described in U.S. Pat. No. 5,175,323) or fatty acid halides (as described in U.S. Pat. No. 4,861,613). The alkoxylated polyol must first be prepared by reacting an epoxide with a polyol such as glycerin, sugar alcohol, glycoside, monosaccharide, disaccharide or other organic compound having two or more hydroxy groups. While such multi-step procedures work well and afford esterified alkoxylated polyols suitable for use as fat substitutes, the number of steps involved, including both synthetic and purification steps, renders these substances considerably more costly than the triglycerides on which they are based. Since the esterified alkoxylated polyol is intended to entirely or substantially replace conventional high caloric triglycerides in food compositions and since certain types of food compositions will normally contain high levels of fat or oil, it is apparent there exists a great need for improved processes whereby the manufacturing cost of esterified alkoxylated polyols may be substantially reduced.

SUMMARY OF THE INVENTION

This invention provides a process for producing a highly esterified alkoxylated polyol composition comprising contacting an epoxide, an alkali metal or alkaline earth salt of a aliphatic polyalcohol, and a triglyceride for a time and at a temperature effective to accomplish ring-opening of the epoxide and formation of fatty acid-esterified oxyalkylene groups. The ratio of the number of moles of epoxide to the total number of moles of triglyceride and aliphatic polyalcohol is from 1:1 to 64:1 and the molar ratio of triglyceride:aliphatic polyalcohol must be at least 9:3/m (more preferably, at least 19:3/m) wherein m is the number of hydroxyl groups in the aliphatic polyalcohol and is typically an integer of from 2 to 8. The process readily affords esterified alkoxylated polyol compositions wherein at least 90% (more preferably, at least 95%) of the end groups are acyl groups rather than hydroxy groups (i.e., the degree of esterification is 90 percent or greater).

The effectiveness of the process of this invention was unexpected since related reactions described in the prior art either require relatively low triglyceride:alcohol ratios or utilize an alkaline catalyst which is a component distinct from the alcohol and not associated with the alcohol as a salt. Moreover, the prior art failed to adequately characterize or describe the structures of the compounds thereby obtained, particularly the degree of esterification achievable. In contrast, we have discovered that by carefully controlling the relative ratios of epoxide, triglyceride, and polyalcohol salt and by deploying the polyalcohol in salt form it is possible to maintain surprisingly high rates of reaction while affording highly esterified products containing low levels of undesired organic impurities, unreacted triglyceride, and unreacted polyalcohol.

DETAILED DESCRIPTION OF THE INVENTION

The triglyceride component which is necessary for the practice of this invention may be any synthetic or naturally-occurring fatty acid triester of glycerin. Such substances will typically correspond to the general structure

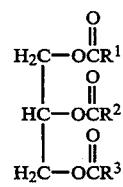

wherein $R^1$, $R^2$, and $R^3$ are the same or different and are $C_5$–$C_{23}$ saturated or unsaturated, linear or branched hydrocarbyl groups (i.e., moieties comprised of carbon and hydrogen atoms). The glycerin may be esterified, for example, with any $C_6$–$C_{24}$ fatty acid such as caproic acid, caprylic acid, pelargonic acid, capric acid, undecylic acid, lauric acid, tridecylic acid, myristic acid, pentadecylic acid, palmitic acid, margaric acid, stearic acid, nonadecylic acid, arachidic acid, ricinoleic acid, behenic acid, lignoceric acid, lauroleic acids, myristoleic acids, palmitoleic acids, oleic acid, elaidic acid, godoleic acid, gondoic acids, cetoleic acid, linoleic acid, linolenic acid, eleostearic acids, and mixtures thereof. Suitable triglycerides include, for example, the triesters of glycerin obtained from natural lipids such as cottonseed oil, soybean oil, peanut oil, olive oil, safflower oil, rapeseed oil (preferably, low erucic rapeseed oil or fully hydrogenated high erucic acid rapeseed oil), sunflower oil, palm oil, palm kernel oil, milk fat, cocoa butter, tallow, lard, fish oils, coconut oil, sesame oil, corn oil, and fully or partially hydrogenated derivatives thereof.

The epoxide to be reacted with the triglyceride may be any organic compound containing a three-membered cyclic ether (oxirane) group and advantageously is a $C_2$–$C_{10}$ aliphatic epoxide. Illustrative epoxides which may be utilized in the instant process include ethylene oxide, propylene oxide, cis- or trans- 2,3-butylene oxide, 1,2-butylene oxide, isobutylene oxide, 1-pentene oxide, cyclohexene oxide, cyclooctene oxide, 1-octene oxide, styrene oxide, allyl glycidyl ether, phenyl glycidyl ether, methyl glycidyl ether, ethyl glycidyl ether, epichlorohydrin, and the like and mixtures thereof. Due to their low cost, high reactivity, and favorable impact on esterified alkoxylated polyol fat substitute properties, the use of ethylene oxide, propylene oxide, 1,2-butylene oxide (also known as 1-butene oxide or 1,2-epoxy butane), or mixtures thereof is especially desirable. The epoxide ring is opened during the process of this invention to afford oxyalkylene units having the general skeletal formula —C—C—O— containing two carbon atoms and one oxygen atom. The oxyalkylene units may be substituted with hydrogen, alkyl, aryl, aralkyl, or other such substituents. In a preferred embodiment, the oxyalkylene units correspond to the structure

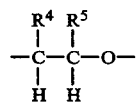

wherein $R^4$ and $R^5$ are the same or different and are hydrogen or a $C_1$–$C_6$ alkyl group such as methyl, ethyl, propyl, isopropyl, butyl, sec-butyl, iso-butyl, tert-butyl, pentyl, hexyl, cyclohexyl, and the like. Most preferably, one of $R^4$ or $R^5$ is methyl and the other R group is hydrogen. In one desirable embodiment, $R^5$ in the oxyalkylene units adjacent to the acyl groups in the final esterified alkoxylated polyol is a $C_1$–$C_6$ alkyl group since secondary ester linkages resistant to enzymatic hydrolysis are thereby furnished.

The amount of epoxide reacted and incorporated into the esterified alkoxylated polyol is selected so as to provide a molar ratio of epoxide:(triglyceride+aliphatic polyalcohol) of from 1:1 to 64:1. When the aliphatic polyalcohol is glycerin, trimethylol propane, 1,2,6-trihydroxyhexane or other trihydric alcohol, it will generally be advantageous to keep the molar ratio in the range of from 3:1 to 20:1. The physical properties and organoleptic qualities of the esterified alkoxylated polyol product may be controlled as desired by varying the amount of epoxide used relative to the amounts of triglyceride and aliphatic polyalcohol. For example, when the epoxide is propylene oxide, increasing the aforementioned ratio will tend to lower the melting point of the esterified alkoxylated polyol.

The other necessary component for practice of the present invention is an alkali metal or alkaline earth metal salt of an aliphatic polyalcohol. To produce a highly esterified alkoxylated polyol composition comparable to that obtained by practice of conventional method (e.g., alkoxylation of a polyol followed by substantially complete esterification), it is critical that the alkali metal or alkaline earth metal be associated with the aliphatic polyalcohol in the salt form and not with some other species as in potassium hydroxide, sodium acetate, potassium methoxide, and the like. The alkali metal is most preferably potassium or sodium. If an alkaline earth metal salt is employed, the alkaline earth metal is most desirably barium or calcium. Potassium salts will typically be preferred over other salts owing to the high rate of reaction and minimal formation of by-products generally attained when such substances are used. The aliphatic polyalcohol (which preferably contains primary or secondary hydroxyl groups and no tertiary hydroxyl groups) may be selected from $C_2$–$C_{10}$ aliphatic diols (e.g., ethylene glycol, propylene glycol, 1,3-propanediol, 1,4-butanediol, 1,2-butanediol, 2,3-butanediol, pinacol, 1,2-cyclohexanediol, 1,2-pentanediol, 1,4-pentanediol, 1,5-pentanediol, 2,4-pentanediol, 3,3-dimethyl-1,2-butanediol, 2-ethyl-2-methyl-1,2-propanediol, 1,2-hexanediol, 1,5-hexanediol, 1,6-hexanediol, 2,5-hexanediol, 2-methyl-2,4-pentanediol, 1,4-cyclohexanediol, 1,7-heptanediol, 2-methyl-1,3-propanediol, 2-methyl-2-propyl-1,3-propanediol, 2,2-diethyl-1,3-propanediol, 2,2-dimethyl-1,3-propanediol (neopentyl glycol) 2,4-dimethyl-2,4-pentanediol, 2-ethyl-1,3-hexanediol, 1,2-octanediol, 1,8-octanediol, 2,2,4-trimethyl-1,2-pentanediol, and the like), $C_3$–$C_{12}$ aliphatic triols (e.g., glycerin, 1,2,4-butanetriol, 2,3,4-pentanetriol, 2-ethyl-2-(hydroxymethyl)-1,3-propanediol (trimethyolpropane), 1,1,1-tris(hydroxymethyl)ethane, 1,2,6-trihydroxyhexane, 1,2,3-heptanetriol, and the like), pentaerythritol, sugar alcohols [including those compounds corresponding to the formula $HOCH_2(CHOH)_nCH_2OH$ wherein n is 2 to 6 such as erythritol, xylitol, sorbitol, arabitol, mannitol, and the like], monosaccharides (e.g., erythrose, threose, ribose, arabinose, xylose, lyxose, allose, altrose, glucose, mannose, gulose, idose, galactose, fructose, galactose, and the like), disaccharides (e.g., sucrose, lactose, maltose) and alkyl glycosides (e.g., methyl glycosides, ethyl glycosides, propyl glycosides, and other glycoside molecules wherein the alkyl glycoside is an acetal formed by interaction of a $C_1$–$C_{20}$ alcohol with a carbonyl group of a mono- or disaccharide such as glucose). Also suitable for use are relatively low molecular weight alkoxylated adducts of the aforementioned $C_2$–$C_{10}$ aliphatic diols, $C_3$–$C_{12}$ aliphatic triols, pentaerythritol, sugar alcohols, monosaccharides, disaccharides, and alkyl glycosides, especially the ethoxylated, propoxylated, and butoxylated adducts having number average molecular weights of from 106 to 500. Examples of such adducts include, but are not limited to, propoxylated glycerin, diethylene glycol, tripropylene glycol, propoxylated sucrose, ethoxylated trimethylol propane, and the like. Also suitable for use as the aliphatic polyalcohol are hydroxy-containing substances such as tetrahydrofuran oligomers, oxetane oligomers, glycerol oligomers, alkoxylated glycerol oligomers, and the like.

The aliphatic polyalcohol will typically contain from 2 to 8 hydroxy groups, which normally will be present as free hydroxy groups (e.g., —OH) or, once the aliphatic polyalcohol is converted into an alkali metal or alkaline earth metal salt, at least one of which will have an alkoxide structure (e.g., —OM, where M=alkali metal, alkaline earth metal). However, some of the hydroxy groups may be present as "masked" hydroxy groups wherein the hydroxy group is substituted with a base-labile functional group such as acyl

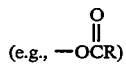
(e.g., —OCR)

which is removed or transferred under the process conditions of this invention, provided that at least one of the hydroxy groups is a free (non-masked) hydroxy group.

For example, the aliphatic polyalcohol may be a mono- or di-ester of glycerin (i.e., a mono- or diglyceride) or any other incompletely esterified polyol such as a partially esterified sugar alcohol, saccharide, diol, triol, tetrol, alkyl glyceride or the like. The ester group may be either a short, medium, long, branched or linear chain, saturated or unsaturated, ester functionality, but preferably is a fatty acid ester group. Mono- and diglycerides and polyols partially substituted with fatty acid ester groups are well-known in the art and may be readily obtained from triglycerides by the direct condensation of fats or fatty acids with glycerin or a similar polyol at an elevated temperature. For example, the process described in British Pat. No. 421,063 may be utilized wherein triglyceride is reacted with the alkali metal salt of glycerin or the like to afford a mixture of the alkali metal salts of mono- and diglycerides. Mixtures of this type may be used as the salt component of the instant invention provided the alkali metal content is sufficiently high. Monoglycerides may be substituted in the 1 or 2 position, while the diglycerides may be 1,3- or 1,2-substituted. Mixtures of various di- and monoglycerides together with glycerol may be utilized to advantage as the aliphatic polyalcohol in the process of this invention.

The salt of the aliphatic polyalcohol may contain from $1/x$ to $m/x$ moles of alkali metal and/or alkaline earth per mole of aliphatic polyalcohol, wherein m is the number of hydroxy groups in the aliphatic polyalcohol and $x=1$ when the salt is an alkali metal salt, and $x=2$ when the salt is an alkaline earth salt. For example, when the aliphatic polyalcohol is glycerin and the salt is a sodium or potassium salt, mono-, di-, and trisodium glycerate or mono-, di-, and tripotassium glycerate or mixtures thereof may be utilized to advantage. In general, higher rates of reaction will be attained as the ratio of alkali metal or alkaline earth to aliphatic polyalcohol is increased. The preparation of alkali metal and alkaline earth salts of aliphatic polyalcohols is well-known in the art. For example, the aliphatic polyalcohol may be contacted with an alkali metal or alkaline earth metal hydroxide, methoxide, or ethoxide and then subjected to vacuum distillation so as to remove water, methanol, or ethanol to form the desired salt. Alternatively, the aliphatic polyalcohol may be reacted with the appropriate number of equivalents of alkali metal (which may be in the form of a solid dispersion or liquid alloy) or alkali metal hydride to form the salt with liberation of hydrogen gas. Generally speaking, the amount of alkali metal or alkaline earth metal present will be from about 250 to 10,000 parts per million (more preferably, from about 1000 to 5000 ppm) based on the total weight of triglyceride, epoxide, and aliphatic polyalcohol.

Since the alkali metal or alkaline earth metal salt of the aliphatic polyalcohol may be a solid, relatively high melting substance with only limited solubility in the other components of the reaction, the process of this invention may be conveniently carried out by forming the salt in situ. For example, the reactor vessel may be initially charged with a mixture of the triglyceride and aliphatic polyalcohol. An alkali metal or alkaline earth metal hydroxide or alkoxide such as sodium hydroxide, potassium hydroxide, barium hydroxide, calcium hydroxide, sodium methoxide, potassium methoxide, sodium ethoxide, potassium t-butoxide, or the like is then added and a vacuum applied so as to remove the water or alcohol generated by the formation of the salt of the aliphatic polyalcohol. The reaction conditions are preferably selected such that the aliphatic polyalcohol is not taken overhead. This procedure is continued until essentially all of the potentially available water or alcohol has been removed. The water or alcohol could also be effectively removed by azeotropic distillation using an appropriate azeotropic agent such as toluene or hexane. Alternatively, an alkali metal or alkaline earth hydride or an alkali metal or alkaline earth in metallic form such as sodium hydride, potassium hydride, calcium hydride, sodium metal, potassium metal, or sodium-potassium alloy could be added so as to react with the aliphatic polyalcohol to form the salt and hydrogen as a by-product, which can be readily removed from the reaction mixture by pulling a vacuum or sparging with an inert gas. This method provides the aliphatic polyalcohol salt (or an equivalent thereof such as the salt of a mono- or diglyceride) in dispersed or dissolved form in a matrix of triglyceride (mono- and di-glycerides may also be simultaneously generated), thus avoiding the handling problems which may otherwise be associated with utilizing the salt in isolated form.

Another possible approach is to carry out an initial base-catalyzed alkoxylation of a aliphatic polyalcohol under conditions such that less than 1 mole of alkali metal or less than 0.5 mole of alkaline earth per mole of aliphatic polyalcohol is present to obtain a relatively low molecular weight product which is a mixture of alkoxylated aliphatic polyalcohol and alkoxylated aliphatic polyalcohol salt. This mixture is then treated with a sufficient amount of an alkali metal, alkaline earth, alkali metal hydroxide, alkaline earth hydroxide, alkali metal alkoxide, alkaline earth alkoxide, alkali metal hydride, alkaline earth hydride, or the equivalent under the appropriate conditions so as to convert the alkoxylated aliphatic polyalcohol to the salt form.

It is critical that the ratio of the number of moles of triglyceride to the number of moles of aliphatic polyalcohol is at least $9:3/m$, wherein m is the number of hydroxy groups in the aliphatic polyalcohol. For example, when an alkali metal salt of glycerin ($m=3$) is employed, this molar ratio must be at least 9:1. Controlling the relative amounts of these two components in this manner permits the direct preparation of highly esterified alkoxylated polyols wherein at least 90% of the end groups in the product are long chain acyl groups. In general, the molar ratio preferably is less than $200:3/m$ since higher ratios may lead to impracticably long reaction times and the generation of undesired by-products. Surprisingly, it is possible and under some circumstances desirable to operate the process of this invention under conditions such that the triglyceride:aliphatic polyalcohol is at least $19:3/m$, as the product thereby obtained can be more than 95% esterified.

The temperature at which the triglyceride, epoxide, and alkali metal or alkaline earth salt of the aliphatic polyalcohol are simultaneously contacted is not critical, but should be selected so as to be sufficiently high to provide a relatively rapid rate of epoxide ring-opening and yet not so high as to generate undesirable by-products such as low molecular weight unsaturated polyethers. Typically, suitable temperatures will be in the range of from 50° C. to 200° C. When propylene oxide, ethylene oxide, and/or 1,2-butylene oxide are utilized as the epoxide and the salt of the aliphatic polyalcohol is a sodium or potassium salt, it is preferred to operate in the range of 80° C. to 150° C.

The reaction mixture is held at the selected temperature sufficiently long so as to accomplish the desired degree of epoxide conversion (i.e., ring-opening) which will generally be at least 75% of the epoxide charged and more preferably is at least 90% of the epoxide charged. At the same time, substantially all (e.g., at least 90%) of the triglyceride and the aliphatic polyalcohol salt will be converted by reaction with the epoxide. Reaction times of from about 0.5 hours to 24 hours will typically suffice for this purpose, but will be dependent on variables such as epoxide reactivity, temperature, alkali metal or alkaline earth concentration, and the like. Optimum reaction times may be readily determined by routine experimentation.

If desired, an inert organic solvent may additionally be present in the reaction mixture so as to dissolve certain of the reaction components, provide effective heat transfer and temperature control, or reduce viscosity. Suitable organic solvents will generally be non-protic substances (i.e., compounds that do not contain active hydrogens) such as aromatic hydrocarbons, aliphatic hydrocarbons, halogenated hydrocarbons, ethers, and the like. The reaction is most preferably carried out under an inert (oxygen-free) atmosphere in the substantial absence of water (i.e., under anhydrous conditions) or alkoxide- or active hydrogen-containing compounds other than the aliphatic polyalcohol salt, as the presence of such substances will detrimentally affect the quality of the highly esterified alkoxylated polyol product. The pressure during the reaction is not critical and may typically be maintained between 0.5 atmospheres and 20 atmospheres. If a relatively volatile epoxide is employed, it will generally be advantageous to use a closed pressurizable reaction vessel so that the bulk of the epoxide may be maintained as a liquid phase in the reactor.

The process of this invention may be carried out in a continuous, semicontinuous, or batch manner using any appropriately configured reactor capable of heating and mixing the reactor contents. Although all of the epoxide may be combined with the triglyceride and aliphatic polyalcohol salt at the beginning of the reaction, it will usually be advantageous to add the epoxide in an incremental fashion to a stirred mixture of the triglyceride and aliphatic polyalcohol salt maintained at the desired reaction temperature. This method of addition will tend to yield a more uniform distribution of oxyalkylene units among the different branches or arms of the esterified alkoxylated polyol and a high degree of triglyceride conversion. Incremental epoxide addition will typically be performed over a 0.5 to 12 hour period, with subsequent soak time to accomplish substantial conversion of the epoxide. If more than one epoxide is utilized, the different epoxides may be added as a mixture or sequentially. By adding ethylene oxide first followed by propylene oxide, the esterified polyoxyalkylene block copolymers the type described in European Pat. Appl. No. 481,717 may be prepared for example.

The process of this invention affords a highly esterified alkoxylated polyol composition characterized by the presence of fatty acid-esterified oxyalkylene groups preferably corresponding to the general structure

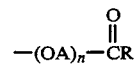

wherein OA is an oxyalkylene group derived from the epoxide, n is an integer of from 1 to 8, and

is a $C_6$–$C_{24}$ saturated or unsaturated acyl group. These fatty-acid esterified oxyalkylene groups are attached through ether linkages to a moiety corresponding to either the starting aliphatic polyalcohol or glycerin. For example, where the aliphatic polyalcohol is glycerin, the moiety is a glyceryl residue

If the aliphatic polyalcohol is a compound other than glycerin, moieties having differing structures will be incorporated into the esterified alkoxylated polyol composition. The composition will also contain a small proportion of unesterified oxyalkylene groups after removal of the alkali metal or alkaline earth having the structure —$(OA)_n$—H, but the proportion of such groups relative to ester groups will be sufficiently minor that the suitability of the composition as a reduced calorie fat substitute will not be adversely affected.

Without wishing to be bound by theory, it is believed that during the operation of the process of this invention acyl group interchange between the triglyceride and the aliphatic polyalcohol takes place. The hydroxyl group or alkoxide group thereby generated in the triglyceride may then undergo alkoxylation by the epoxide to form hydroxy-terminated oxyalkylene groups. These oxyalkylene groups may then in turn be re-esterified by subsequent acyl group transfer from other species present in the reaction mixture. At the same time, hydroxy groups in the aliphatic polyalcohol are alkoxylated and then esterified by means of an acyl group interchange reaction. The net result is that the oxyalkylene groups derived by ring-opening of the epoxide are inserted between the glyceryl moiety and the fatty acid acyl groups of the triglyceride.

When the reaction of the epoxide, triglyceride, and aliphatic polyalcohol has proceeded to the extent desired, the alkali metal or alkaline earth present may be removed by any appropriate method. For example, the reaction product can be contacted with a particulate absorbent such as magnesium or aluminum silicate at an appropriate temperature (typically, 50° C. to 150° C.) so as to absorb the alkali metal or alkaline earth onto the absorbent and then filtered. Small amounts of water may be added so as to enhance absorption efficiency. Alternatively, the reaction product can be treated with an acid such as a mineral acid (e.g., hydrochloric acid, sulfuric acid, phosphoric acid) or an organic acid (e.g., acetic acid, oxalic acid, citric acid, tartaric acid) so as to form a precipitate which can be removed by filtration. Treatment with an appropriate ion exchange resin or carbon dioxide or extraction with water, dilute aqueous acid, a polar solvent such as methanol, or the like may also be utilized.

The reduced calorie fat substitute produced by the process of this invention can be additionally purified or treated so as to render it more suitable for use in food compositions using any of the techniques known in the art for refining natural vegetable or animal oils and fats. Such techniques include, but are not limited to, degumming, bleaching, filtration, deodorization, hydrogenation, deacidification, steam stripping, dewaxing, and the like. Various additives such as stabilizers, anti-oxidants, vitamins and so forth can also be incorporated into the esterified alkoxylated polyol. If a completely or more completely esterified product is desired, the esterified alkoxylated polyol may be reacted under appropriate conditions with a fatty acid, fatty acid ester, fatty acid halide, or other fatty acid equivalent so as to convert the hydroxyl groups present to long chain acyl groups.

Esterified alkoxylated polyol compositions produced in accordance with this invention are oil-like or fat-like substances which are substantially insoluble in water and which can replace, in full or in part, conventional edible oils or fats in a cooking oil, frying oil, salad oil, or shortening, for example. Additional uses include combining the reduced calorie fat substitutes with other foodstuff ingredients to form foods such as frozen desserts (e.g., sherbert, ice cream, frozen yogurt, milk shakes), baked goods (cakes, doughnuts, muffins, brownies, breads, pies, rolls, pastries, cookies, biscuits, crackers), nut butters (peanut butter), dairy products (margarine, sour cream, coffee lighteners, cheese, cheese spreads, flavored dips, filled cream, filled milk), mayonnaise, salad dressing, savory snacks (potato chips, corn chips, cheese puffs, pretzels, fried foods (fried poultry, fritters, fried pies, fried vegetables such as french fried potatoes, fried fish), reformed and comminuted meats (lunch meats, sausage, hot dogs, hamburger), pet foods, meat and egg substitutes or extenders, whipped toppings, gravies and other sauces, frostings, fillings, icings, cocoa butter replacements or blends, candies and confectionaries (especially those normally containing fatty ingredients such as chocolate or peanut butter), soups and dry baking mixes (for muffins, cakes, pancakes, waffles, brownies, and the like). Owing to the fat-like properties and stability of the esterified alkoxylated polyols, minimum reformulation of standard food recipes will generally be required. The viscosity, melting profile, yield point, hardness, thixotropic area, liquid/solid stability, solid fat index, and other physical properties of the reduced calorie fat substitute are preferably selected by manipulation of the chemical structures and relative proportions of the individual starting materials of the process such that the product mimics as closely as possible the analogous properties of the conventional high caloric triglyceride being replaced.

Illustrative ingredients which may be used in combination with the highly esterified alkoxylated polyol compositions obtainable by practice of this invention include carbohydrates (flour, starches, sugars, celluloses, polydextrose or other bulking agents), edible lipids (triglycerides), proteins (from animal or vegetable sources), vitamins, antioxidants, emulsifiers, thickeners, preservatives, colorants, flavors, fragrances, sugar substitutes (saccharin, aspartame, sucralose, cyclamates, and the like), other fat substitutes or fat mimetics (for example, sucrose polyester (olestra), sorbitol polyester, or caprenin), water, milk, spices, eggs and the like. Oil-in-water to water-in-oil emulsions can be readily prepared by combining water, the reduced calorie fat substitute, and other ingredients such as emulsifiers. The reduced calorie fat substitutes produced using this invention are particularly suitable for the preparation of foods requiring exposure to elevated temperatures. Unlike other proposed fat substitutes such as proteinacious macrocolloids or certain polysaccharide-based substances requiring water to render them fat-like in texture, the highly esterified alkoxylated polyol compositions produced by this invention are exceptionally stable thermally and do not readily decompose or lose their fat-like properties when heated. The compositions thus may readily be utilized in deep fat frying applications to prepare fried foods such as savory snacks, fried chicken, fried fish, french fries, and the like since they will function as effective heat transfer media (that is, they will transmit heat rapidly and uniformly to the food being fried and also provide crispness).

From the foregoing description, one skilled in the art can readily ascertain the essential characteristics of this invention and, without departing from the spirit and scope thereof, can make various changes and modifications of the invention to adapt it to various usages, conditions, and embodiments.

The following examples further illustrate the process of this invention, but are not limitative of the invention in any manner whatsoever.

EXAMPLE 1

This example demonstrates that the process of this invention may be used to directly produce a highly esterified alkoxylated polyol composition from a triglyceride.

A suitably sized autoclave equipped with paddle stirrer is charged with soybean oil (990 parts by weight) and the monopotassium salt of glycerin (10 parts by weight). The mixture is heated under a nitrogen atmosphere to a temperature of 110° C. Propylene oxide (584 parts by weight) is then added continuously over a 6 hour period. When addition is completed, the mixture is maintained at 110° C. for another 4 hours or at least until 90% conversion of the propylene oxide is achieved. Magnesium silicate (30 parts by weight) is added and the mixture stirred for 2 hours at 120° C. The reaction mixture is cooled to ca. 50° C. and filtered to remove the magnesium silicate containing absorbed potassium, yielding the highly esterified alkoxylated polyol composition. The composition is expected to contain ca. 8 oxypropylene units per equivalent of glycerin and to be ca. 97% esterified (i.e., ca. 3% of the end-groups present in the composition as a whole are hydroxy groups, with ca. 97% of the end-groups being acyl groups).

EXAMPLE 2

A suitably sized autoclave equipped with paddle stirrer is charged with glycerin (920 parts by weight) and potassium hydroxide (38.2 parts by weight). The mixture is heated at 110° C. and 10 mm pressure until no additional water is evolved. Propylene oxide (1740 parts by weight) is then incrementally added at a temperature of 100° C. so as to maintain a pressure of 50–60 psig. After addition of the propylene oxide is completed, the reaction mixture is maintained at 100° C. until substantially all of the epoxide is consumed.

The mixture is cooled to 30° C. and potassium methoxide (654 parts by weight) added slowly with stirring. Methanol is removed by heating at 100° C. under vacuum (10 mm), yielding the potassium salt of propoxylated glycerin containing about 3 moles of propylene oxide per mole of glycerin.

A suitably sized autoclave equipped with paddle stirrer is charged with hydrogenated high erucic rapeseed oil (900 parts by weight), corn oil (100 parts by weight), and the potassium salt of propoxylated glycerin prepared hereinabove (12 parts by weight). The mixture is heated under a nitrogen atmosphere to a temperature of 120° C. and propylene oxide (348 parts by weight) added continuously at a rate so as to maintain an autogenous pressure of 50–60 psig. When addition is completed, the mixture is heated at 120° C. until substantially all of the propylene oxide is reacted. The highly esterified alkoxylated polyol composition thus obtained is purified as described in Example 1. The composition is expected to contain ca. 6 oxypropylene units per equivalent of glycerin and to be >95% esterified.

A suitably sized autoclave equipped with paddle stirrer is charged with coconut oil (740 parts by weight) and the mono- and di- glyceride sodium salt mixture described hereinabove (15.9 parts by weight). The mixture is heated under a nitrogen atmosphere to a temperature of 100° C. and propylene oxide (174 parts by weight) added continuously at a rate so as to maintain an autogenous pressure of 50–60 psig. When addition is complete, the reaction temperature is increased to 120° C. and held at that temperature until at least 95% of the propylene oxide has reacted. The highly esterified alkoxylated polyol composition thus obtained is purified as described in Example 1. The composition is expected to contain ca. 3 oxypropylene units per equivalent of glycerin and to be >95% esterified.

EXAMPLES 4–13

These examples illustrate the use of various epoxides, triglycerides, and salts of aliphatic polyalcohols in the process of this invention. The procedures of Examples 1–3 are generally followed, with the substitutions noted in Table I. In each case, the reaction mixture is maintained at temperature following epoxide addition until at least 95% of the epoxide has reacted.

TABLE 1

| Example No. | Epoxide | pbw[1] | Triglyceride | pbw | Aliphatic Polyalcohol | pbw | M[2] | ppm | Temp., °C. |
|---|---|---|---|---|---|---|---|---|---|
| 4 | ethylene oxide | 660 | corn oil | 1000 | trimethylolpropane | 4.5 | K | 1560 | 80 |
| 5 | 1-butene oxide | 360 | peanut oil | 1000 | 1,2,6-trihydroxy hexane | 5.4 | Na | 1350 | 100 |
| 6 | propylene oxide | 696 | fully hydrogenated high erucic rapeseed oil[3] | 1000 | glycerin | 4.4 | Ca | 1120 | 125 |
| 7 | PO/EO[5] 1:1 | 510 | partially hydrogenated soybean oil[4] | 1000 | glycerin monostearate | 14.3 | Ba | 3600 | 140 |
| 8 | PO/BO[6] 2:1 | 564 | cottonseed oil | 1000 | propylene glycol | 5.1 | K | 3330 | 90 |
| 9 | propylene oxide | 174 | sunflower seed oil | 1000 | 1,4-butanediol | 4.6 | K | 1650 | 100 |
| 10 | propylene oxide | 1160 | safflower seed oil | 1000 | pentaerythritol | 4.5 | K | 1200 | 115 |
| 11 | 1-octene oxide | 512 | coconut oil | 1000 | 2,3-butanediol | 4.5 | Na | 1510 | 130 |
| 12 | ethylene oxide | 352 | palm oil | 1000 | propoxylated glycerin | 9.7 | Na | 1870 | 95 |
| 13 | propylene oxide | 870 | lard | 1000 | glucose | 5.1 | Na | 770 | 115 |

FOOTNOTES, Table I
[1]parts by weight
[2]designates the alkali metal or alkaline earth present in the salt of the aliphatic polyalcohol
[3]iodine value less than 1
[4]iodine value = 30
[5]PO = propylene oxide; EO = ethylene oxide; added as a 1:1 mole:mole mixture
[6]PO = propylene oxide; BO = 1,2-butylene oxide; PO added and reacted first, followed by BO; PO:BO mole:mole ratio = 2:1 fied.

EXAMPLE 3

Sodium (4.0 parts by weight) is added to glycerin (220 parts by weight) and the mixture heated and stirred at 50° C. until the sodium is dissolved. The resulting mixture (comprised of ca. 20 parts by weight of the sodium salt of glycerin and 204 parts by weight glycerin) is then mechanically agitated with peanut oil (1000 parts by weight) while heating rapidly to 200° C. After 15 minutes at 200° C., a mixture of mono- and di-glycerides is obtained. Additional sodium (127.4 parts by weight) is added with stirring after cooling to 40° C. and the resulting mixture agitated until the sodium is dissolved to afford the sodium salt of a mono- and di-glyceride mixture.

I claim:
1. A process for producing a highly esterified alkoxylated polyol composition comprising contacting an epoxide, an alkali metal or alkaline earth salt of an aliphatic polyalcohol, and a triglyceride for a time and at a temperature of from 50° C. to 200° C. to accomplish ring-opening of the epoxide and formation of fatty acid esterified oxyalkylene groups, wherein the molar ratio of epoxide:(triglyceride+aliphatic polyalcohol) is from 1:1 to 64:1 and the molar ratio of triglyceride:aliphatic polyalcohol is at least 9:3/m wherein m is the number of hydroxy groups in the aliphatic polyalcohol and is an integer of from 2 to 8.
2. The process of claim 1 wherein the epoxide is a $C_2$–$C_{10}$ aliphatic epoxide.

3. The process of claim 1 wherein the triglyceride is a triester of glycerin and a $C_6$-$C_{24}$ fatty acid selected from caproic acid, caprylic acid, pelargonic acid, capric acid, undecylic acid, lauric acid, tridecylic acid, myristic acid, pentadecylic acid, palmitic acid, margeric acid, stearic acid, nonadecylic acid, arachidic acid, ricinoleic acid, behenic acid, lignoceric acid, lauroleic acids, myristoleic acids, palmitoleic acids, oleic acid, elaidic acid, godoleic acids, gondoic acids, cetoleic acids, linoleic acid, linolenic acid, eleostearic acids, and mixtures thereof.

4. The process of claim 1 wherein the alkali metal or alkaline earth salt of the aliphatic polyalcohol is a sodium or potassium salt.

5. The process of claim 1 wherein the aliphatic polyalcohol is selected from $C_2$-$C_{10}$ aliphatic diols, $C_3$-$C_{12}$ aliphatic triols, pentaerythritol, sugar alcohols, monosaccharides, disaccharides, and alkyl glycosides.

6. The process of claim 1 wherein the temperature is from 80° C. to 150° C.

7. The process of claim 1 wherein the fatty acid-esterified oxyalkylene groups have the general structure

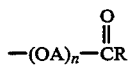

wherein OA is an oxyalkylene unit derived from the epoxide, n is an integer of from 1 to 8, and

is a $C_6$-$C_{24}$ saturated or unsaturated acyl group.

8. The process of claim 1 wherein m is 3 and the molar ratio of epoxide:(triglyceride+aliphatic polyalcohol) is from 3:1 to 20:1.

9. The process of claim 1 wherein the concentration of alkali metal or alkaline earth is from 500 to 10,000 parts per million based on the total combined weight of epoxide, alkali metal or alkaline earth salt of aliphatic polyalcohol, and triglyceride.

10. The process of claim 1 wherein the highly esterified alkoxylated polyol composition has a degree of esterification greater than 95 percent.

11. The process of claim 1 wherein the aliphatic polyalcohol is glycerin, a monoglyceride, a diglyceride, or a mixture thereof.

12. The process of claim 1 wherein the aliphatic polyalcohol has a number average molecular weight of from 106 to 500 and is an alkoxylated $C_2$-$C_{10}$ aliphatic diol, an alkoxylated $C_3$-$C_{12}$ aliphatic triol, an alkoxylated pentaerythritol, an alkoxylated sugar alcohol, an alkoxylated monosaccharide, an alkoxylated disaccharide, an alkoxylated alkyl glycoside, a tetrahydrofuran oligomer, an oxetane oligomer, a glycerol oligomer, or an alkoxylated glycerol oligomer.

13. The process of claim 1 wherein the molar ratio of triglyceride:aliphatic polyalcohol is at least 19:3/m.

14. A process for producing a highly esterified alkoxylated polyol composition comprising contacting a $C_2$-$C_{10}$ aliphatic epoxide, an alkali metal salt of an aliphatic polyalcohol having 3 hydroxy groups, and a triglyceride at a temperature of from 50° C. to 200° C. for a time effective to accomplish ring-opening of the $C_2$-$C_{10}$ aliphatic epoxide and formation of fatty acid-esterified oxyalkylene groups, wherein the molar ratio of $C_2$-$C_{10}$ aliphatic epoxide:(triglyceride+aliphatic polyalcohol) is from 3:1 to 20:1 and the molar ratio of triglyceride:aliphatic polyalcohol is at least 19:1 and less than 200:1.

15. The process of claim 14 comprising the additional step of removing the alkali metal from the highly esterified alkoxylated polyol composition.

16. The process of claim 14 wherein the $C_2$-$C_{10}$ aliphatic epoxide is selected from ethylene oxide, propylene oxide, 1,2-butylene oxide, and mixtures thereof.

17. The process of claim 14 wherein the triglyceride is a triester of glycerin obtained from a natural lipid selected from cottonseed oil, soybean oil, peanut oil, olive oil, safflower oil, rapeseed oil, sunflower oil, palm oil, palm kernel oil, milk fat, cocoa butter, tallow, lard, coconut oil, sesame oil, fish oils, corn oil, fully or partially hydrogenated derivatives thereof, and mixtures thereof.

18. The process of claim 14 wherein the concentration of alkali metal is from 1000 to 5000 parts per million based on the total combined weight of epoxide, alkali metal salt of aliphatic polyalcohol, and triglyceride.

19. The process of claim 14 wherein the fatty acid-esterified oxyalkylene groups have the general structure

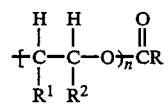

wherein $R^1$ and $R^2$ are the same or different and are selected from hydrogen, methyl, or ethyl, n is an integer of from 1 to 6, and

is an $C_6$-$C_{24}$ saturated or unsaturated acyl group.

20. The process of claim 14 wherein said process is carried out in the absence of water and any alkoxide or hydroxy group-containing species other than the alkali metal salt of the aliphatic polyalcohol.

21. The process of claim 14 wherein the alkali metal salt of the aliphatic polyalcohol is a potassium salt of glycerin, a monoglyceride, a diglyceride, an alkoxylated glycerin having a number average molecular weight of from 133 to 500, or a mixture thereof.

22. The process of claim 13 wherein the epoxide is propylene oxide.

23. A process for producing a highly esterified alkoxylated polyol composition comprising contacting an epoxide selected from ethylene oxide, propylene oxide, 1,2-butylene oxide, or a mixture thereof, a potassium salt of an aliphatic polyalcohol selected from glycerin, monoglycerides, diglycerides, and alkoxylated glycerins having number average molecular weights of from 133 to 500, and a triglyceride at a temperature of from 80° C. to 150° C. for a time effective to accomplish ring-opening of the epoxide and formation of fatty acid-esterified oxyalkylene groups, wherein the molar ratio of epoxide:(triglyceride+aliphatic polyalcohol) is from 3:1 to 20:1, the molar ratio of triglyceride:aliphatic polyalcohol is at least 19:1 and less than 200:1, and the potassium is present at a concentration of from 1000 to 5000 parts per million based on the combined weight of epoxide, the potassium salt of the aliphatic polyalcohol, and the triglyceride.

* * * * *